United States Patent [19]
Gosselin et al.

[11] Patent Number: 5,505,737
[45] Date of Patent: Apr. 9, 1996

[54] QUICK RELEASE COUPLING FOR A DISSECTING TOOL

[75] Inventors: Norman J. Gosselin; William W. McKinney, both of Fort Worth, Tex.

[73] Assignee: Midas Rex Pneumatic Tools, Inc., Fort Worth, Tex.

[21] Appl. No.: 270,016

[22] Filed: Jul. 1, 1994

[51] Int. Cl.⁶ ................................................. A61B 17/00
[52] U.S. Cl. .................................. 606/79; 606/80
[58] Field of Search ........................... 606/79, 80, 167, 606/170, 172, 173, 180; 433/128, 129; 81/177.85; 408/224

[56] References Cited

U.S. PATENT DOCUMENTS

| Re. 27,032 | 7/1964 | Hall . | |
|---|---|---|---|
| 2,525,669 | 10/1950 | Hainault | 606/80 |
| 2,842,131 | 7/1958 | Smith | 606/80 |
| 4,319,577 | 3/1982 | Bofinger | 408/224 |
| 4,362,161 | 12/1982 | Reimels | 606/80 |
| 4,963,155 | 10/1990 | Lazzeri et al. . | |
| 5,222,956 | 6/1993 | Waldron | 606/80 |
| 5,265,343 | 11/1993 | Pascaloff . | |
| 5,330,480 | 7/1994 | Meloul | 606/80 |
| 5,380,333 | 1/1995 | Meloul | 606/80 |

OTHER PUBLICATIONS

The Hall Surgical Drill Instruction Manual.
YNET Motordrill Operating Procedures Pamphlet.
MicroAire Surgical Instruments Sales Brochure.
Mednext Sales Brochure.
Stryker Instruments Sales Brochure.
Meisinger Chirurgie Surgery Order Brochure.
OSM Chirurgie Surgery Order Brochure.
Product information sheet and three photographs for surgical drill system of Hall Ultra Power High Speed Drill.

*Primary Examiner*—Michael A. Brown
*Attorney, Agent, or Firm*—James E. Bradley; Grady K. Bergen

[57] ABSTRACT

A coupling device is used for attaching a dissecting tool to a rotary shaft of a surgical instrument. The device is comprised of a spindle attachment which secures to a spindle of the rotary shaft. The spindle attachment has a shaft engagement portion for engaging the shaft of the dissecting tool. The shaft engagement portion is provided with apertures which terminate within a central bore of the engagement portion through which the tool shaft extends. Surrounding the spindle attachment is a sleeve which has a contact surface which contacts spherical locking members located within the apertures of the shaft engagement portion. A sleeve engagement member is coupled to the base and has an external surface configured to allow a user to grasp the sleeve so that it can be moved between retracted and extended positions. As the sleeve engagement member is moved between the retracted and extended positions, it causes the sleeve to be move to an engaged or disengaged position. When moved to the engaged position, the contact surface of the sleeve forces the locking members into the central bore where the locking members contact the shaft of the dissecting tool, preventing movement of the dissecting tool within the socket of the spindle. The sleeve can then be moved to a disengaged position wherein the spherical locking members are allowed to retract within the apertures, allowing the dissecting tool to be removed from the socket.

19 Claims, 3 Drawing Sheets

5,505,737

QUICK RELEASE COUPLING FOR A DISSECTING TOOL

BACKGROUND OF THE INVENTION

1. Field of the Invention

The present invention relates in general to surgical instruments for use in the dissection of bone and other tissue. In particular, the present invention relates to a quick release coupling device for securing a cutting tool to the rotary shaft of a rotary machine.

2. Summary of the Prior Art

Surgical tools for use in the dissection of bone and tissue during surgical procedures are conventional in the art. Many such tools employ pneumatic or electrical motors to rotate the cutting element of a dissecting tool. In their most basic form, such surgical instruments comprise a motor portion having a rotary shaft, a dissecting tool having a cutting element which is rotated by the motor, a sleeve to surround and support the dissection tool, and means for connecting the dissecting tool to a spindle or collet of the rotary shaft. The spindle or collet of the rotary shaft is usually housed within a base which is attached to the motor.

In order to change or replace the cutting tool, the base is disconnected or removed from the motor so that the collet can be accessed. A collet nut is usually provided with the collet in order to secure the shaft of the dissecting tool within a recess or socket of the collet. The collet nut must be removed or loosened from the spindle with the use of a wrench or other tool in order for the cutting tool to be removed. Once the cutting tool is replaced, the collet nut is re-attached to the spindle and the base resecured.

Because it is often necessary to replace the cutting tool many times during a given surgical procedure, the procedure just described must be carried out frequently. This is often a time-consuming task due to the rod and wrench steps necessary to replace the cutting tool. What is needed is a means for coupling a cutting tool to a spindle or a rotary shaft of a motor which can be quickly and-easily removed and replaced.

SUMMARY OF THE INVENTION

A surgical cutting tool is releasably secured to a rotatable shaft of a rotary machine. The rotatable shaft is housed within a base and has a recess or socket for receiving a tool shaft of the cutting tool. An aperture formed in the rotatable shaft extends radially outward from and is in communication with the recess. A sleeve surrounds the rotary shaft and is movable between an engaged and disengaged position. At least one locking member locates and is free to move within the aperture of the rotatable shaft.

A sleeve engagement member is coupled to the base and is movable between an extended and retracted position. The sleeve engagement member engages the sleeve, when moved between the extended and retracted positions, to cause the sleeve to be moved between the engaged and disengaged positions. The sleeve engagement member has an external surface which is configured to allow a user to grasp the sleeve engagement member so that the sleeve engagement member can be moved between the retracted and extended positions.

When the sleeve is moved to the engaged position, the locking member is contacted by the sleeve so that the locking member protrudes into the recess or socket of the rotatable shaft and engages the tool shaft of the cutting tool. The tool shaft is thereby secured within the recess.

To remove the cutting tool, the sleeve is moved to the disengaged position by means of the sleeve engagement member which causes the sleeve to disengage the locking member. This allows the locking member to retract within the aperture from the recess so that the tool shaft of the cutting tool can be removed from the socket.

DETAILED DESCRIPTION OF THE INVENTION

Figure 1:
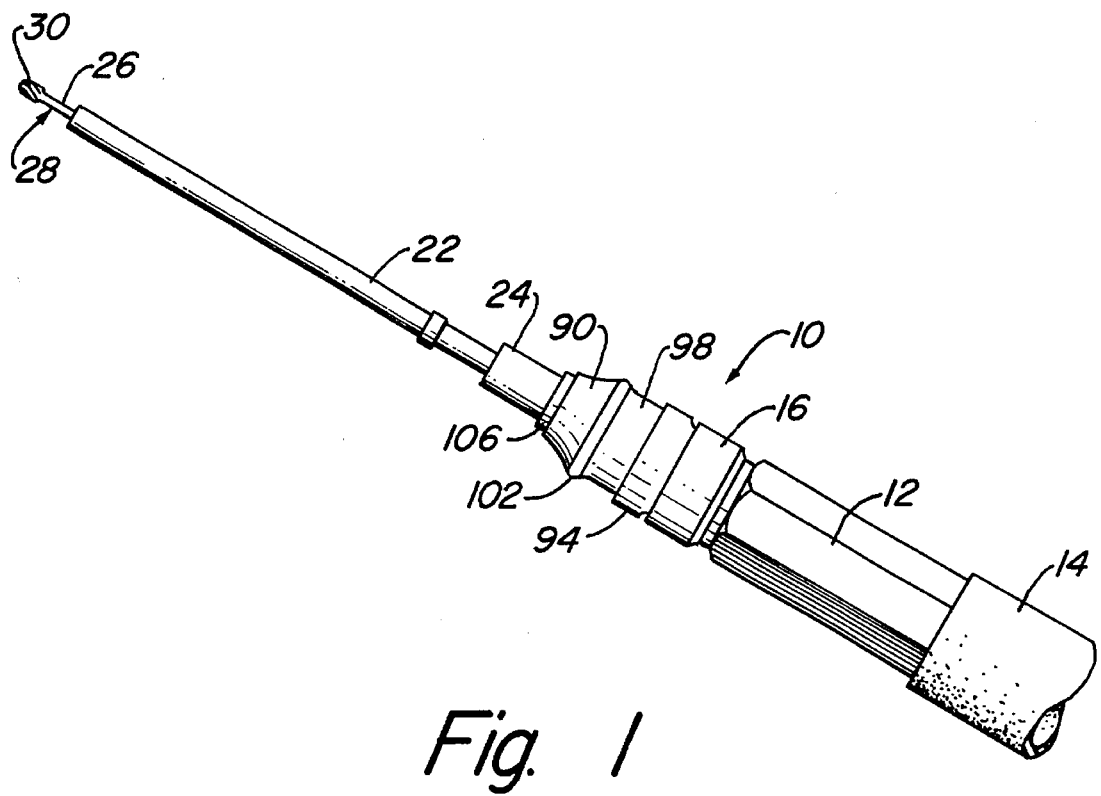
FIG. 1 is a side view of a surgical instrument constructed in accordance with the invention.

Referring to FIG. 1, a surgical instrument 10 used for the removal and cutting of tissue in surgical procedures is shown. The surgical instrument 10 is provided with a fluid driven motor 12 having an air conduit 14 which provides a source of pressurized air to the motor 12. Attached to the motor 12 is a base 16 which is coupled to a threaded neck 18 of the motor 12 by means of threads 20 (FIGS. 2 and 3).

A support sleeve 22 extends from and is joined at an end 24 of the base 16 opposite the threaded neck 18. The support sleeve 22 houses a tool shaft 26 of a dissecting tool 28. At one end of the dissecting tool 28 is a cutting element 30. The cutting element 30 can be a burr, saw blade or drill used in the cutting or removing of tissue. The sleeve 22 may be provided with internal bearings (not shown) to support the tool shaft 26 as the dissecting tool 28 is rotated.

Figure 2:
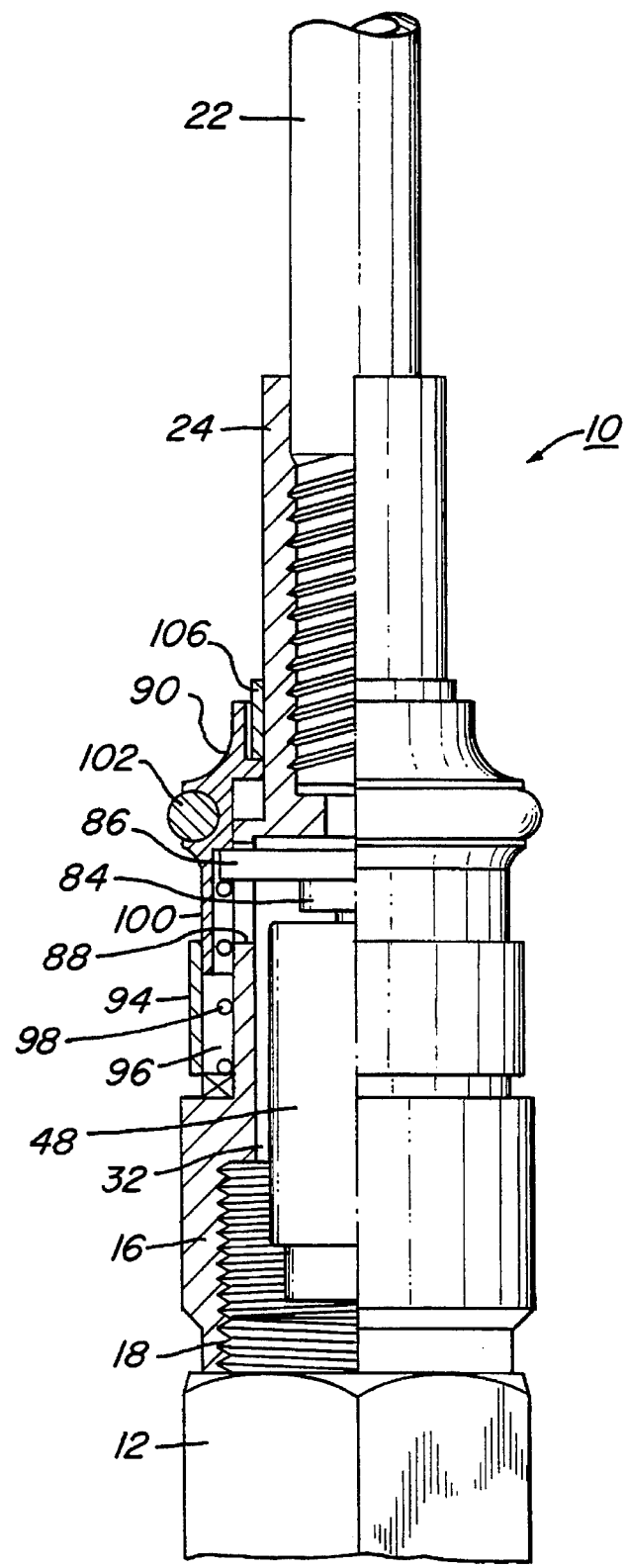
FIG. 2 is a partial cross-sectional side view of the surgical instrument of FIG. 1 showing a coupling device for securing a cutting tool of the surgical instrument to a rotary shaft and constructed in accordance with the invention.
Figure 3:
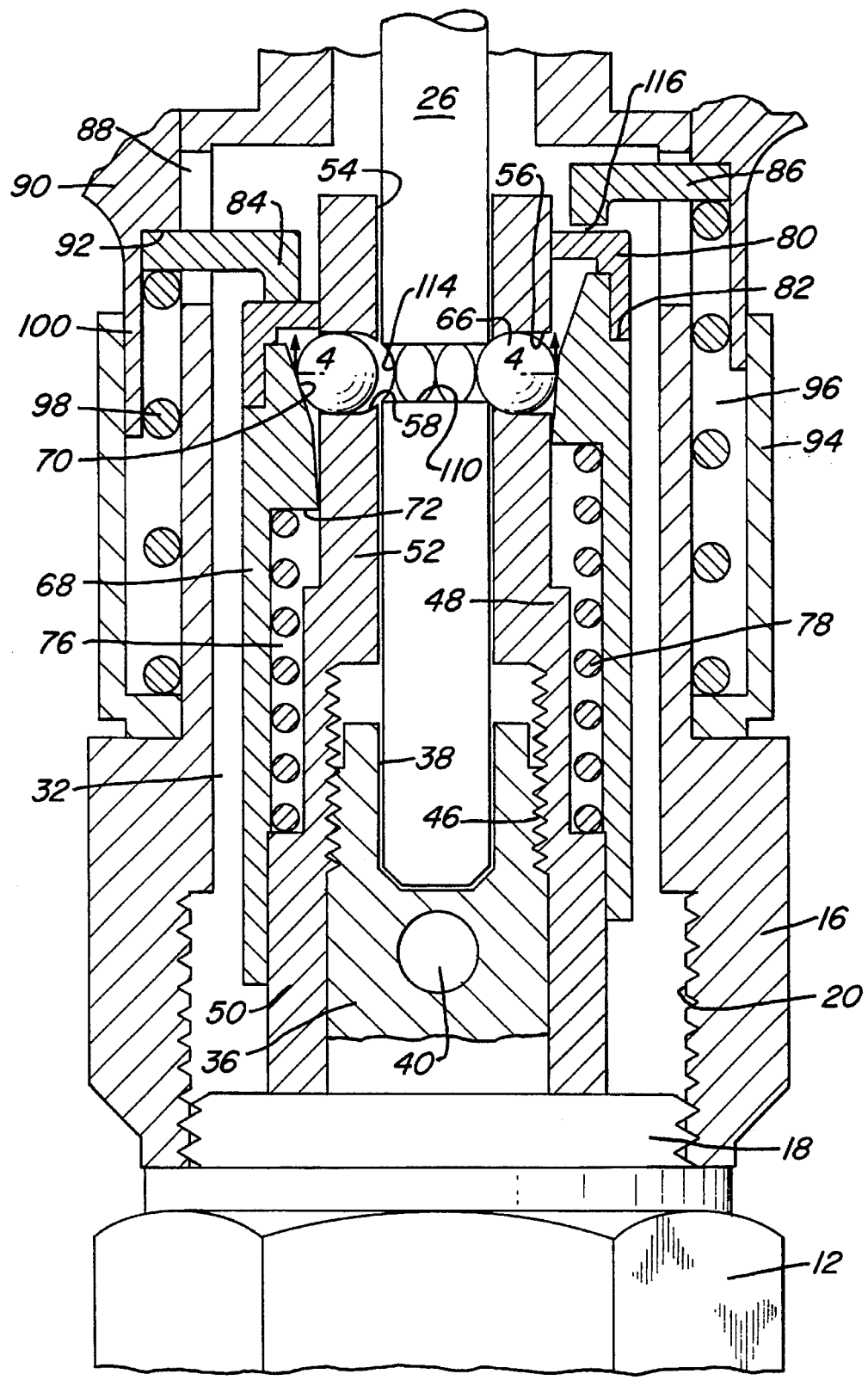
FIG. 3 is an enlarged cross-sectional side view of the surgical instrument of FIG. 1, showing the left side in a release position and the right side in a locked position.

Referring to FIGS. 2 and 3, the base 16 is provided with a cavity 32. Extending from the neck 18 of the motor 12 is a rotary shaft or spindle 36 of conventional design. The shaft 36 is rotated by the motor 12 about a longitudinal axis. The shaft 36 has a elongated recess or socket 38 for receiving the end of the tool shaft 26 opposite the cutting element 30 of the dissecting tool 28 for rotating the tool 28 about the longitudinal axis. As used herein, the descriptive terms "longitudinal" or "longitudinally" are with reference to the longitudinal axis of the shaft 36. At the base of the shaft 36 is a hole 40. Formed on the exterior of the shaft 36 are helical threads 46.

A shaft attachment 48 which replaces a conventional shaft attachment has a lower, shaft engagement portion 50 and is provided with internal threads for engaging the threads 46 of the shaft 36 so that the shaft attachment 48 securely couples to the shaft 36. The threads of the shaft attachment 48 and shaft 36 should be oriented to ensure that they do not become uncoupled during rotation of the shaft attachment 48 when operating the instrument 10. Located opposite the shaft engagement portion 50 of the shaft attachment 48 is a cylindrical shaft engagement portion 52. As can be seen in FIG. 3, the exterior of the shaft engagement portion 52 is substantially parallel with the longitudinal axis of the shaft 36. Formed in the shaft engagement portion 52 of the shaft attachment 48 is a central bore 54 for receiving the tool shaft 26 of the dissecting tool 28. The central bore 54 is concentric with the socket or recess 38 of the shaft 36.

Formed in the shaft engagement portion 52 are a plurality of substantially cylindrical apertures 56 which extend radially outward from the central bore 54 to the exterior of the shaft engagement portion 52 to provide communication therebetween. The apertures 56 are located around the entire circumference of the shaft engagement portion 52. Each aperture 56 decreases in diameter towards the central bore 54 to form a conical locking member seat 58.

Located within the apertures 56 are spherical locking members or balls 66 (FIG. 3). The balls 66 are free to roll or move within the apertures 56, but are prevented from fully entering the central bore 54 by the locking member seat 58 located at the inner edge of the apertures 56.

Encircling the shaft attachment 48 is a cylindrical sleeve 68. The lower end of the sleeve 68 closely receives the shaft engagement portion 50 of the shaft attachment 48 so that the sleeve 68 slides along the exterior of shaft attachment 48 for a distance when moved between engaged and disengaged positions along lines parallel to the longitudinal axis of the shaft 36. FIG. 3 shows a split view of the sleeve 68, with the left side of the sleeve 68 being in the disengaged position and the right side being in the engaged position. As used herein, the terms "upper," "lower", "left" and "right" are with reference to the instrument 10 as shown and oriented in FIGS. 2 and 3. It should be understood that these terms are used merely for convenience in this description and in no way should be construed as limitations. In operation, the whole sleeve 68 is moved between one or the other positions. Located at the upper end and protruding radially inward from the inner wall of the sleeve 68 is an annular contact surface 70 which longitudinally overlaps the apertures formed in the shaft engagement portion 52 of the shaft attachment 48. The contact surface 70 is wedge-shaped and slopes radially inward from the upper end of the contact surface 70 to the lower end. As can be seen in FIG. 3, the lower end of the contact surface 70 touches or nearly touches the exterior wall of the shaft engagement portion 52. The lower end of the contact surface 70 terminates in a downward facing annular shoulder 72 which protrudes radially inward from the inner wall of the sleeve 68.

The shaft engagement portion 50 of the shaft attachment 48 has an upward facing shoulder 74 which faces toward the shoulder 72 of the sleeve 68. The inner wall of the sleeve 68 is spaced apart from the exterior of the shaft engagement portion 52 of the shaft attachment 48 to define an annular space 76. Located within this annular space 74 surrounding the shaft attachment 48 is an outwardly biased coiled spring 98 which abuts the lower facing shoulder 72 of the sleeve 68 at one end and the upper facing shoulder 74 of the shaft attachment 48 at the other end. The coiled spring 98 urges the sleeve 68 upward to the engaged position, as seen in FIG. 3.

At the upper end of the sleeve 68 is a sleeve cap 80 which is joined to and seats against a recessed annular upper shoulder 82 of the sleeve 68. The sleeve cap 80 has a central opening for receiving the shaft engagement portion 52 of the shaft attachment 48. Located directly above the sleeve cap 80 and surrounding the shaft engagement portion 52 of the shaft attachment 48 is a sleeve contact ring 84. The sleeve contact ring 84 is provided with two tabs 86 which project laterally from opposite sides of the contact ring 84 through elongated slots 88 formed in the base 16.

Mounted around the base 16 is a sleeve engagement collar 90. The sleeve engagement collar 90 is longitudinally movable relative to the base 16 and is provided with an annular, lower facing shoulder 92. Positioned below the collar 90 is a cylindrical spring housing 94 which surrounds and is joined at its lower end to the base 16. The wall of the spring housing 94 is spaced apart from the exterior of the base 16 to define an annular space 96 for receiving the lower end of an outer coiled spring 98 which surrounds the base 16. As can be seen in FIGS. 2 and 3, the collar 90 has a lower cylindrical portion or skirt 100 which surrounds the upper end of the coiled spring 98 and is received within the spring housing 94. The lower skirt 100 of the collar 90 should be able to slide within the spring housing 94 for a distance as the collar 90 is moved in relation to the base 16.

The coiled spring 98 is outwardly biased and contacts the lower surface of the tabs 86 so that the tabs 86 seat against the shoulder 92 of the collar 90. The force of the spring 98 against the tabs 86 and shoulder 92 urges the collar 90 upward to an extended position where the collar 90 is prevented from further movement by a retaining ring 106 secured to the base 16. As seen in FIG. 2, the collar 90 has an outward protruding annular shoulder 102 which is configured to allow a user to easily grasp the collar 90 so that the collar 90 can be moved longitudinally relative to the base 16.

Figure 4:
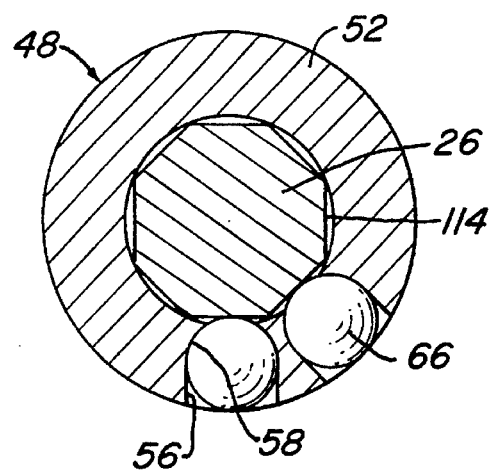
FIG. 4 is a partial cross-sectional view of the cutting tool of FIG. 1, taken along the line 4—4 of FIG. 3, and showing locking members engaging a shaft of the cutting tool constructed in accordance with the invention.

The tool shaft 26 of the dissecting tool 28 is provided with a cut-out portion 110 which extends around the circumference of the tool shaft 26. The cut-out portion 110 is formed by a series of transverse cylindrical shaped recesses 114 which intersect with each other so that the cut-out portion 110 has a substantially octagonal transverse cross section, as shown in FIG. 4. The cylindrical recesses 114 have a radius of curvature substantially equal to the radius of the spherical locking members 66. The cut-out portion 110 is located at a point along the length of the shaft 26 so that it aligns longitudinally with the apertures 56 of the shaft attachment 48 when the tool shaft 26 is fully inserted into the socket 38 of the shaft 36.

The operation of the quick release device is as follows. Initially, the sleeve 68 is in the engaged position. In the engaged position, the lower portion of the sloped contact surface 70 of the sleeve 68 contacts and wedges each locking member 66 against the seat 58 of each of the apertures 56. The locking members 66 prevent further upward movement of the sleeve 68 caused by the force of the spring 78. When seated against the seat 58 of the apertures 56, each locking member 66 protrudes for a distance within the interior of the central bore 54 of the shaft engagement portion 52 of the shaft attachment 48. The seat 58 prevents the locking members 66 from fully entering the central bore 54.

Referring to FIG. 2, prior to inserting the tool shaft 26 of the dissecting tool 28 through the sleeve 22 (FIG. 1) and into the socket 38 of the shaft 36, a user grasps the sleeve engagement collar 90 by means of the protruding shoulder 102. By pulling the sleeve engagement collar 90 downward towards the motor 12 to a retracted position, the collar 90 compresses the outer spring 98 so that the skirt 100 is retracted into the spring housing 94 and causes the contact ring 84 to engage the sleeve cap 80 of the sleeve 68 so that the sleeve 68 is forced downward to the disengaged position, compressing the coiled spring 98. In the disengaged position, the upper end of the contact surface 70 of the sleeve 68, which is spaced furthest from the apertures 56 of the shaft engagement portion 52, longitudinally overlaps the apertures 56 so that the locking members 66 can move freely within each aperture 56, away from the seat 58 and out of the central bore 54. When the sleeve 68 is in this disengaged position, the upper end of the contact surface 70 of the sleeve 68 is spaced close enough to the apertures 56 to loosely retain the locking members 66 within the apertures 56.

The tool shaft 26 of the dissecting tool 28 may then be inserted through the support sleeve 22, through the central bore 54 of the shaft attachment 48 and into the socket 38 of the shaft 36. Because the locking members 66 are free to move within the apertures 56 when the sleeve 68 is in the disengaged position, the tool shaft 26 forces the balls 66 away from the central bore 54 as it is being inserted.

When the tool shaft 26 is fully inserted into the socket 38 of the shaft 36, the user releases the collar 90. The outer spring 98 forces the collar 90 and contact ring 84 upward to the extended position. Simultaneously, as the collar 90 and contact ring 84 are forced upward by the outer spring 98, the coiled spring 98 forces the sleeve 68 to the engaged position. This causes the lower end of the sloped contact surface 70 to force the locking members 66 through the apertures 56 and into the central bore 54 and against the recessed areas 114 of the cut-out portion 110 of the tool shaft 24. This effectively prevents the tool shaft 24 from rotation and longitudinal movement within the socket 38 of the shaft 36. When the collar 90 is in the extended position and the sleeve 68 is in the engaged position, the contact ring 84 is spaced apart from the sleeve cap 80 and sleeve 68, forming a gap or clearance 116. This allows the sleeve 68 and sleeve cap 80 to rotate freely along with the shaft attachment 48, shaft 36 and tool shaft 26 when the surgical instrument 10 is operated in a conventional manner.

When it is necessary to change or replace the dissecting tool 28, the collar 90 is moved to the retracted position as previously described. This forces the sleeve 68 to the disengaged position and allows the locking members 66 to retract from the central bore 54 within the apertures 56 so that the tool shaft 26 may be removed from the shaft 36 and replaced.

The device of the invention has several advantages. Because the shaft attachment and sleeve can be attached to a conventional shaft, pre-existing rotary machines can be utilized without additional modification. It is not necessary to remove the base of the surgical instrument, as in prior art methods, in order to access the shaft to remove or replace the dissecting tool. The coupling device of the invention allows easy removal and replacement of the cutting tools in a much shorter period of time.

While the invention has been shown in only one of its forms, it should be apparent to those skilled in the art that it is not so limited, but is susceptible to various changes without departing from the scope of the invention.

We claim:

1. In a surgical instrument for cutting and removing tissue, the instrument having a rotary motor which drives a rotary cutting tool, the rotary cutting tool having a cutting end and a tool shaft for coupling to the motor, the motor having a rotary shaft with a recess for receiving the tool shaft of the cutting tool and a base which surrounds the rotary shaft, the improvement comprising:

a sleeve which surrounds the rotary shaft and is movable between a first and a second position;

a sleeve engagement member which is coupled to the base and is moveable between a retracted and extended position, the sleeve engagement member engaging the sleeve when moved between the retracted and extended positions to cause the sleeve to be moved between the first and second positions, the sleeve engagement member having an external surface which is configured to allow a user to manually grasp the sleeve engagement member so that the sleeve engagement member can be moved between the retracted and extended positions; and at least one locking member which locates and is movable within an aperture of the rotary shaft, the aperture being in communication with the recess, the locking member being contacted by the sleeve when the sleeve is moved to the first position so that the locking member protrudes into the recess of the rotary shaft and engages the tool shaft of the cutting tool to secure the tool shaft within the recess; and wherein the sleeve is disengaged from the locking member when moved to the second position to allow the locking member to retract so that the tool shaft of the cutting tool can be removed from the recess.

2. The instrument of claim 1, further comprising:

biasing means for urging the sleeve to the first position.

3. The instrument of claim 1, further comprising:

biasing means for urging the sleeve engagement member to one of the retracted and extended positions.

4. The instrument of claim 1, wherein the rotary shaft comprises:

a spindle having a socket; and a spindle attachment which secures to the spindle and has a central bore which is concentric with the socket of the spindle, the tool shaft of the cutting tool being received within the bore and socket, and wherein the aperture is located in the spindle attachment and is in communication with the bore.

5. The instrument of claim 1, wherein:

the locking member has a spherical configuration.

6. The instrument of claim 1, wherein:

the sleeve is movable between the first and second positions along lines parallel to a longitudinal axis of the rotary shaft; and the sleeve has an inner contact surface for contacting the locking member, at least a portion of the contact surface sloping radially inward in the direction of movement of the sleeve when the sleeve is moved from the first position to the second position.

7. The instrument of claim 1, further comprising:

retaining means for retaining the locking member within the aperture while allowing a portion of the locking member to protrude into the recess for a predetermined distance.

8. A device for releasably securing a surgical cutting tool to a rotary shaft of a rotary machine, the rotary machine having a base which surrounds the rotary shaft and the rotary shaft having a recess for receiving a tool shaft of the cutting tool, the rotary shaft, the device comprising in combination:

a sleeve which surrounds the rotary shaft and is movable between a first and a second position;

a sleeve engagement member which is coupled to the base and moveable between a retracted and extended position, the sleeve engagement member engaging the sleeve when moved between the retracted and extended positions to cause the sleeve to be moved between the first and second positions, the sleeve engagement member having an external surface which is configured to allow a user to manually grasp the sleeve engagement member so that the sleeve engagement member can be moved between the retracted and extended positions;

first biasing means for urging the sleeve to the first position;

second biasing means for urging the sleeve engagement member to one of the retracted and extended positions; and at least one locking member which locates and is movable within an aperture of the rotary shaft which extends radially outward from the recess, the locking member being contacted by the sleeve when the sleeve is moved to the first position so that the locking member protrudes into the recess of the rotary shaft and engages the tool shaft of the cutting tool to secure the tool shaft within the recess; and wherein the sleeve is disengaged from the locking member when moved to the second position to allow the locking member to retract so that the tool shaft of the cutting tool can be removed from the recess.

9. The device of claim 8, wherein:

the first biasing means is a coiled spring which surrounds the rotary shaft and abuts against the sleeve member.

10. The device of claim 8, wherein:

the second biasing means is a coiled spring which surrounds the base and abuts against the sleeve engagement member.

11. The device of claim 8, wherein the rotary shaft comprises:

a spindle having a socket; and a spindle attachment which secures by threads to the spindle and has a central bore which is concentric with the socket of the spindle, the tool shaft of the cutting tool being received within the bore and socket, and wherein the aperture is located in the spindle attachment and terminates within the bore.

12. The instrument of claim 8, wherein:

the locking member has a spherical configuration.

13. The instrument of claim 8, wherein:

the sleeve is movable between the first and second positions along lines parallel to a longitudinal axis of the rotary shaft; and the sleeve has an inner contact surface for contacting the locking member, at least a portion of the contact surface sloping radially inward in the direction of movement of the sleeve when the sleeve is moved from the first position to the second position.

14. The instrument of claim 8, further comprising:

retaining means for retaining the locking member within the aperture while allowing a portion of the locking member to protrude into the recess for a predetermined distance.

15. A device for releasably securing a surgical cutting tool to a rotary machine, the rotary machine having a base which houses a spindle, the spindle being recessed to receive a tool shaft of the cutting tool, the device comprising in combination:

a spindle attachment which secures to the spindle of the rotary machine, the spindle attachment having a shaft engagement portion with a bore which is concentric with the recess of the spindle for receiving the tool shaft of the cutting tool when the tool shaft is inserted into the recess of the spindle, the engagement portion having an aperture which communicates with and extends radially outward from the bore;

a sleeve which surrounds the spindle attachment, the sleeve being movable between a first and a second position along an axis of the spindle;

a sleeve engagement member which is coupled to the base and is moveable between a retracted and extended position, the sleeve engagement member having a sleeve contact portion which surrounds the spindle attachment and has transverse tabs which extend through elongated slots formed in the base, the sleeve contact portion engaging the sleeve when the sleeve engagement member is moved between the retracted and extended positions to cause the sleeve to be moved between the first and second positions, the sleeve engagement member having an external surface which is configured to allow a user to manually grasp said external surface of the sleeve engagement member so that the sleeve engagement member can be moved between the retracted and extended positions;

a first spring for urging the sleeve to the first position;

a second spring for urging the sleeve engagement member to one of the extended and retracted positions; and at least one locking member which locates and is movable within the aperture of the spindle attachment, the locking member being contacted by the sleeve when the sleeve is moved to the first position so that the locking member protrudes into the bore of the spindle attachment and engages the tool shaft of the cutting tool to secure the tool shaft within the recess of the spindle, the spindle attachment, sleeve and locking member rotating with the spindle when the rotary machine is operated; and wherein the sleeve is disengaged from the locking member when moved to the second position to allow the locking member to retract so that the tool shaft of the cutting tool can be removed from the recess.

16. The instrument of claim 15, wherein:

the locking member has a spherical configuration.

17. The instrument of claim 15, wherein:

the sleeve is movable between the first and second positions along lines parallel to a longitudinal axis of the spindle; and the sleeve has an inner contact surface for contacting the locking member, at least a portion of the contact surface sloping radially inward in the direction of movement of the sleeve when the sleeve is moved from the first position to the second position.

18. The instrument of claim 15, further comprising:

retaining means for retaining the locking member within the aperture while allowing a portion of the locking member to protrude into the recess for a predetermined distance.

19. A method for removably securing a rotary cutting tool to a rotary motor of a surgical instrument used for cutting and removing tissue, the rotary cutting tool having a cutting end and a tool shaft for coupling to the motor, the motor having a rotary shaft with a recess for receiving the tool shaft of the cutting tool and a base which surrounds the rotary shaft, the method comprising the steps of:

forming an aperture in the rotary shaft which communicates with the recess;

locating at least one locking member within the aperture of the rotary shaft so that the locking member is free to move within the aperture;

providing a sleeve which surrounds the rotary shaft and is movable between a first and second position;

coupling a sleeve engagement member to the base so that the sleeve engagement member is moveable between a retracted and extended position;

providing the sleeve engagement member with an external surface which is configured to allow a user to manually grasp the sleeve engagement member;

manually grasping the sleeve engagement member;

moving the sleeve engagement member to one of the retracted and extended positions so that the sleeve engagement member engages the sleeve and causes the sleeve to be moved between a first position wherein the sleeve contacts the locking member so that the locking member protrudes into the recess of the rotary shaft and engages the tool shaft of the cutting tool to secure the tool shaft within the recess; and then moving the sleeve engagement member to the other of the retracted and extended positions so that the sleeve engagement member is moved to the second position wherein the sleeve is disengaged from the locking member to allow the locking member to retract so that the tool shaft of the cutting tool can be removed from the recess.

* * * * *